(12) United States Patent
Li et al.

(10) Patent No.: US 10,973,613 B2
(45) Date of Patent: Apr. 13, 2021

(54) MULTILAYER DENTAL APPLIANCES AND RELATED METHODS AND SYSTEMS

(71) Applicant: ALIGN TECHNOLOGY, INC., San Jose, CA (US)

(72) Inventors: Chunhua Li, Cupertino, CA (US); Yan Chen, Cupertino, CA (US); Heinz Pudleiner, Krefeld (DE); Klaus Meyer, Dormagen (DE); Joerg Nickel, Dormagen (DE); Craig Pehlert, Lenox, MA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 150 days.

(21) Appl. No.: 15/476,655

(22) Filed: Mar. 31, 2017

(65) Prior Publication Data
US 2017/0202641 A1  Jul. 20, 2017

Related U.S. Application Data

(62) Division of application No. 13/470,681, filed on May 14, 2012, now Pat. No. 9,655,691.

(51) Int. Cl.
*A61C 7/08* (2006.01)
*B32B 27/28* (2006.01)
(Continued)

(52) U.S. Cl.
CPC ............... *A61C 7/08* (2013.01); *B29C 51/14* (2013.01); *B32B 7/02* (2013.01); *B32B 25/08* (2013.01);
(Continued)

(58) Field of Classification Search
CPC .. A61C 7/08; B29C 51/14; B32B 7/02; B32B 27/40; B32B 25/08; B32B 25/20;
(Continued)

(56) References Cited

U.S. PATENT DOCUMENTS 2,467,432 A   4/1949  Kesling
3,407,500 A  10/1968  Kesling
(Continued)

FOREIGN PATENT DOCUMENTS

AU    3031677 A    5/1979
AU     517102 B2   7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Jacob T Minskey
*Assistant Examiner* — Caroline Montiel
(74) *Attorney, Agent, or Firm* — Wilson Sonsini

(57) ABSTRACT

A dental appliance for positioning a patient's teeth includes a removable orthodontic tooth positioning appliance having teeth receiving cavities shaped to directly receive at least some of the patient's teeth and apply a resilient positioning force to the patient's teeth. The appliance includes a hard polymer layer having a hard polymer layer elastic modulus disposed between a first soft polymer layer having a first soft polymer layer elastic modulus and a second soft polymer layer having a second soft polymer layer elastic modulus. The hard polymer layer elastic modulus is greater than each of the first soft polymer layer elastic modulus and the second soft polymer layer elastic modulus. At least one of the first soft polymer layer and the second soft polymer layer has a flexural modulus of greater than about 35,000 psi.

22 Claims, 8 Drawing Sheets

(51) Int. Cl.
  *B32B 25/08* (2006.01)
  *B32B 27/08* (2006.01)
  *B32B 27/30* (2006.01)
  *B32B 27/34* (2006.01)
  *B32B 27/36* (2006.01)
  *B32B 27/40* (2006.01)
  *B32B 7/02* (2019.01)
  *B29C 51/14* (2006.01)
  *B29K 67/00* (2006.01)
  *B29K 75/00* (2006.01)
  *B32B 25/20* (2006.01)
  *B32B 27/32* (2006.01)
  *B29L 31/00* (2006.01)

(52) U.S. Cl.
  CPC .............. *B32B 25/20* (2013.01); *B32B 27/08* (2013.01); *B32B 27/281* (2013.01); *B32B 27/285* (2013.01); *B32B 27/286* (2013.01); *B32B 27/308* (2013.01); *B32B 27/32* (2013.01); *B32B 27/34* (2013.01); *B32B 27/36* (2013.01); *B32B 27/365* (2013.01); *B32B 27/40* (2013.01); *B29K 2067/00* (2013.01); *B29K 2075/00* (2013.01); *B29K 2995/007* (2013.01); *B29K 2995/0026* (2013.01); *B29K 2995/0077* (2013.01); *B29K 2995/0082* (2013.01); *B29L 2031/753* (2013.01); *B32B 2250/03* (2013.01); *B32B 2250/24* (2013.01); *B32B 2274/00* (2013.01); *B32B 2307/412* (2013.01); *B32B 2307/536* (2013.01); *B32B 2307/54* (2013.01); *B32B 2307/546* (2013.01); *B32B 2323/04* (2013.01); *B32B 2323/10* (2013.01); *B32B 2367/00* (2013.01); *B32B 2371/00* (2013.01); *B32B 2375/00* (2013.01); *B32B 2377/00* (2013.01); *B32B 2535/00* (2013.01); *B32B 2555/00* (2013.01)

(58) Field of Classification Search
  CPC ..... B32B 27/08; B32B 27/281; B32B 27/286; B32B 27/308; B32B 27/32; B32B 27/34; B32B 27/36; B32B 27/365; B32B 2250/24; B32B 2307/54; B32B 2250/03; B32B 2274/00; B32B 2307/412; B32B 2307/536; B32B 2535/00; B32B 2307/546; B29K 2995/0077; B29K 2067/00; B29K 2075/00; B29K 2995/0026; B29K 2995/007; B29K 2995/0082; B29L 2031/753
  See application file for complete search history.

(56) References Cited

U.S. PATENT DOCUMENTS

| | | |
|---|---|---|
| 3,600,808 A | 8/1971 | James |
| 3,660,900 A | 5/1972 | Lawrence |
| 3,683,502 A | 8/1972 | Melvin |
| 3,738,005 A | 6/1973 | Cohen et al. |
| 3,763,109 A | 10/1973 | Witsiepe et al. |
| 3,766,146 A | 10/1973 | Witsiepe et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,346,195 A | 8/1982 | Hornbaker et al. |
| 4,348,178 A | 9/1982 | Kurz |
| 4,410,595 A | 10/1983 | Matsumoto et al. |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,791,156 A * | 12/1988 | Hostettler .............. C08G 18/42 433/199.1 |
| 4,793,803 A | 12/1988 | Martz |
| 4,798,534 A | 1/1989 | Breads |
| 4,824,723 A | 4/1989 | Campbell et al. |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,024,790 A | 6/1991 | Grossman et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |

(56) References Cited

U.S. PATENT DOCUMENTS

| | | | |
|---|---|---|---|
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et el. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,390,812 B1 | 5/2002 | Chishti et al. |
| 6,398,548 B1 | 6/2002 | Muhammad et al. |
| 6,402,707 B1 | 6/2002 | Ernst |
| 6,454,565 B2 | 9/2002 | Phan et al. |
| 6,482,298 B1 | 11/2002 | Bhatnagar |
| 6,485,298 B2 | 11/2002 | Chishti et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,667,101 B2 | 12/2003 | Silagy et al. |
| 6,705,861 B2 | 3/2004 | Chishti et al. |
| 6,705,863 B2 | 3/2004 | Phan et al. |
| 6,722,880 B2 | 4/2004 | Chishti et al. |
| 6,746,757 B1 | 6/2004 | Takagi et al. |
| 7,121,825 B2 | 10/2006 | Chishti et al. |
| 7,201,575 B2 | 4/2007 | Adell et al. |
| 7,354,270 B2 | 4/2008 | Abolfathi et al. |
| 7,641,828 B2 | 1/2010 | Desimone et al. |
| 8,235,713 B2 | 8/2012 | Phan et al. |
| 8,496,473 B2 | 7/2013 | Phan et al. |
| 9,655,691 B2 | 5/2017 | Li et al. |
| 9,655,693 B2 | 5/2017 | Li et al. |
| 10,052,176 B2 | 8/2018 | Li et al. |
| 2001/0041320 A1 | 11/2001 | Phan et al. |
| 2002/0006597 A1 | 1/2002 | Andreiko et al. |
| 2002/0146549 A1 | 10/2002 | Kranenburg-Van Dijk et al. |
| 2002/0192617 A1 | 12/2002 | Phan et al. |
| 2003/0009252 A1 | 1/2003 | Pavlovskaia et al. |
| 2003/0139834 A1 | 7/2003 | Nikolskiy et al. |
| 2003/0190576 A1 | 10/2003 | Phan et al. |
| 2003/0224311 A1 | 12/2003 | Cronauer |
| 2004/0128010 A1 | 7/2004 | Pavlovskaia et al. |
| 2004/0146670 A1 | 7/2004 | Chin et al. |
| 2004/0170941 A1 | 9/2004 | Phan et al. |
| 2005/0055118 A1 | 3/2005 | Nikolskiy et al. |
| 2005/0100853 A1 | 5/2005 | Tadros et al. |
| 2007/0148608 A1 | 6/2007 | Tadros et al. |
| 2007/0231765 A1 | 10/2007 | Phan et al. |
| 2008/0020337 A1 | 1/2008 | Phan et al. |
| 2008/0230938 A1 | 9/2008 | Grefenstein et al. |
| 2008/0248438 A1 | 10/2008 | Desimone et al. |
| 2008/0299507 A1 | 12/2008 | Li et al. |
| 2009/0087808 A1 | 4/2009 | Soo et al. |
| 2009/0130438 A1 | 5/2009 | Nassi et al. |
| 2009/0239188 A1 | 9/2009 | Ting et al. |
| 2009/0246724 A1* | 10/2009 | Chen ............... A61C 7/08 433/6 |
| 2009/0298006 A1 | 12/2009 | Schwartz |
| 2009/0306327 A1 | 12/2009 | Stewart et al. |
| 2010/0055639 A1 | 3/2010 | Lewis et al. |
| 2011/0020761 A1 | 1/2011 | Kalili |
| 2011/0062609 A1* | 3/2011 | DeSimone ............ A61C 7/08 264/16 |
| 2011/0069134 A1 | 3/2011 | Sakagami et al. |
| 2012/0315484 A1 | 12/2012 | Riedl et al. |
| 2015/0140300 A1* | 5/2015 | Pudleiner ............ B32B 27/08 428/215 |
| 2015/0374464 A1 | 12/2015 | Stewart |
| 2016/0228215 A1 | 8/2016 | Li et al. |
| 2017/0007362 A1 | 1/2017 | Chen et al. |
| 2019/0159870 A1 | 5/2019 | Li et al. |
| 2019/0183611 A1 | 6/2019 | Li et al. |
| 2019/0231484 A1 | 8/2019 | Li et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| DE | 102004014023 A1 | 10/2005 |
| DE | 102010009230 A1 | 8/2011 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 15500777 | 8/1979 |
| JP | S5358191 A | 5/1978 |
| JP | H0428359 A | 1/1992 |
| JP | H06256630 A | 9/1994 |
| JP | 08508174 | 9/1996 |
| JP | H08508174 A | 9/1996 |
| JP | 2011079284 A | 4/2011 |
| RU | 2201944 C2 | 4/2003 |
| RU | 2008137623 A | 3/2010 |
| WO | WO-9008512 A1 | 8/1990 |
| WO | WO-9104713 A1 | 4/1991 |
| WO | WO-9410935 A1 | 5/1994 |
| WO | WO-9711106 A1 | 3/1997 |
| WO | WO-9832394 A1 | 7/1998 |
| WO | WO-9844865 A1 | 10/1998 |
| WO | WO-9858596 A1 | 12/1998 |
| WO | WO-0180762 A2 | 11/2001 |
| WO | WO-0180764 A1 | 11/2001 |

(56) References Cited

FOREIGN PATENT DOCUMENTS

| WO | WO-2004041898 A1 | 5/2004 |
|---|---|---|
| WO | WO-2006096558 A2 | 9/2006 |
| WO | WO-2010043419 A1 | 4/2010 |
| WO | WO-2010074789 A1 | 7/2010 |
| WO | WO-2013172812 A1 | 11/2013 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Andrews, The Six Keys to Optimal Occlusion Straight Wire, Chapter 3, pp. 13-24 (No Date Given).

Baird Equity Research. Align Technology, Inc. (ALGN): Analyst Day Recap. May 30, 2014. 12 pages.

Baird Equity Research. Align Technology, Inc. (ALGN): Impressive Quarter/Guide, Momentum Stronger than We Realized. Oct. 18, 2013. 15 pages.

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.," Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Biostar Opeation & Training Manual. Great Lakes Orthodontics, Ltd. 199 Fire Tower Drive, Tonawanda, New York. 14150-5890, 20 pages total (No Date Given).

Blu, et al., "Linear interpolation revitalized", IEEE Trans. Image Proc., 13(5):710-719 (May 2004.

Boedeker.com. Polycarbonate specifications [retrieved on Sep. 10, 2013]. Retrieved from the Internet: http://www.boedeker.com/polyc_p.htm.

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the lnvisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on The Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

Cardinal Industrial Finishes, Powder Coatings information posted at< http://www.cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside," Part 2 F. Duret—A Man with a Vision, Part 3 The Computer Gives New Vision—Literally, Part 4 Bytes 'N Bites—The Computer Moves from the Front Desk to the Operatory, Canadian Dental Journal, vol. 54 (9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992.

(56) References Cited

OTHER PUBLICATIONS

Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dentrac Corporation, Dentrac document, pp. 4-13 (No Date Given).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
DuraClearTM product information, Allesee Orthodontic Appliances—Pro Lab, 1 page (No Date Given).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
International Preliminary Report on Patentability dated Nov. 18, 2014 for International PCT Patent Application No. PCT/US2012/037745.
International Search Report and Written Opinion dated Jan. 30, 2013 for International PCT Patent Application No. PCT/US2012/037745.
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Lubrizol.com. I sop last 2530 data sheet [retrieved on Sep. 10, 2013]. Retrieved from the Internet: http://www.lubrizol.com/Medicai/TDS/Isoplast-2530.pdf.
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).

(56) References Cited

OTHER PUBLICATIONS

Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Plastics.ides.com. Polyurethane Thermoset Elastomer Typical Properties Generic [retrieved on Jul. 27, 2014]. Retrieved from the Internet: http://plastics.ides.com/generics/57/c/t/polyurethane-thermoset-elastomer-tsu- properties-processing.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www. essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et a/., "CAD/CAM for Dental Restorations—Some of the Curious Challenges," IEEE Trans. Biomed. Eng., 38(4):344-345 (Apr. 1991.
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System In Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Siemens, "CEREC—Computer-Reconstruction," High Tech in der Zahnmedizin, 14 pages total (No Date Given).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stifel. TAM Survey. Properly Aligning Expectations Ahead of 4Q13 Guidance. Align Technology, Inc. Oct. 10, 2013. 12 pages.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice Is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile!Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
Tru-Tain Orthodontic & Dental Supplies, Product Brochure, Rochester, Minnesota 55902, 16 pages total (No Date Given).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).

(56) References Cited

OTHER PUBLICATIONS

Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).
You May Be A Candidate For This Invisible No-Braces Treatment, Allesee Orthodontic Appliances-Pro Lab product information for patients, 2 pages (No Date Given).
Co-pending U.S. Appl. No. 16/043,065, filed Jul. 23, 2018.
Co-pending U.S. Appl. No. 16/264,420, filed Jan. 31, 2019.
International search report with written opinion dated Jun. 28, 2013 for PCT/EP2013/059701.
Bayer Corporation, "Texin® 990R," pp. 1-4, Nov. 2002, Pittsburgh, PA.
Campo, E. A. "Mechanical Properties of Polymeric Materials," from "Selection of Polymeric Materials: Plastics Design Library," 2008, 4 pages.
Co-pending U.S. Appl. No. 16/835,101, filed Mar. 30, 2020.
Emblem, A. "Plastics properties for packaging materials," from "Packaging Technology: Fundamentals, Materials and Processes," 2012, 3 pages.
"Polycarbonate," Encyclopaedia Britannica, Aug. 24, 2017, 1 page, URL: https://www.britannica.com/science/polycarbonate.
Material Data Sheet of Ecdel 9966. 3 pages total (Year: 2020).
"Overview of Materials for PETG Copolyester" 2 pages (http://www.nnatweb.conn/search/DataSheet.aspx?MatGUID=4de1c85bb946406a86c52b688e3810d0&ckck=1) (webpage retrieved on Oct. 27, 2020) (Year: 2020).
Larson, Kent "Can You Estimate Modulus From Durometer Hardness for Silicones?" Dow White Paper, 2019 The Dow Chemical Company, Form No. 11-3716-01A S2D, pp. 1-5.

* cited by examiner

MULTILAYER DENTAL APPLIANCES AND RELATED METHODS AND SYSTEMS

CROSS-REFERENCE

This application is a divisional of U.S. patent application Ser. No. 13/470,681, filed May 14, 2012, now U.S. Pat. No. 9,655,691, issued May 23, 2017, the entire contents of which are incorporated herein by reference.

BACKGROUND OF THE INVENTION

The present invention generally relates to the field of orthodontics, and more particularly to the design of multi-layer dental positioning appliances.

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and reactive adjustments to the braces by the practitioner, the appliances to move the teeth toward their final destination.

More recently, alternatives to conventional orthodontic treatment with traditional affixed appliances e.g., braces) have become available. For example, systems including a series of preformed appliances/aligners have become commercially available from Align Technology, Inc., San Jose, Calif., under the trade name Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ software from Align Technology, Inc. The design of the aligners relies on computer modeling of the patient's teeth in a series of planned successive tooth arrangements, and the individual aligners are designed to be worn over the teeth, such that each aligner exerts force on the teeth and elastically repositions the teeth to each of the planned tooth arrangements.

While recently developed orthodontic treatment technologies, such as those described above, represent a considerable advancement in the field of orthodontics, additional advancements remain of interest. For example, in some instances it may be advantageous to develop materials that improve properties of the appliances/aligners used for orthodontic treatment. As such, there is a need for shell aligners that can, for example, produce more continuous force and better bring a patient's teeth into a desired occlusion.

BRIEF SUMMARY OF THE INVENTION

The present invention provides multilayer orthodontic positioning appliances, as well as related methods and systems. The disclosed multilayer appliances include a removable orthodontic tooth positioning appliance having teeth receiving cavities shaped to directly receive at least some of the patient's teeth and apply a resilient positioning force to the patient's teeth. The multilayer appliances can include a hard polymer layer disposed between two soft polymer layers. The multilayer dental appliances of the present invention, among many aspects, provide, for example, improved material performance, stress relaxation properties and longer working range. In addition, the mechanical properties of the materials and appliances described herein can improve orthodontic treatments by, for example, reducing the need for midcourse corrections during treatment and the number of aligners used for a given treatment.

The disclosed methods include methods for making multilayer dental appliances. The disclosed systems including a plurality of appliances having teeth receiving cavities shaped to directly receive at least some of the patient's teeth and apply a resilient positioning force to the patient's teeth. The appliances can be successively worn by a patient to move teeth from one arrangement to a successive arrangement. At least one of the appliances in the system can include a hard polymer layer disposed between two soft polymer layers.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
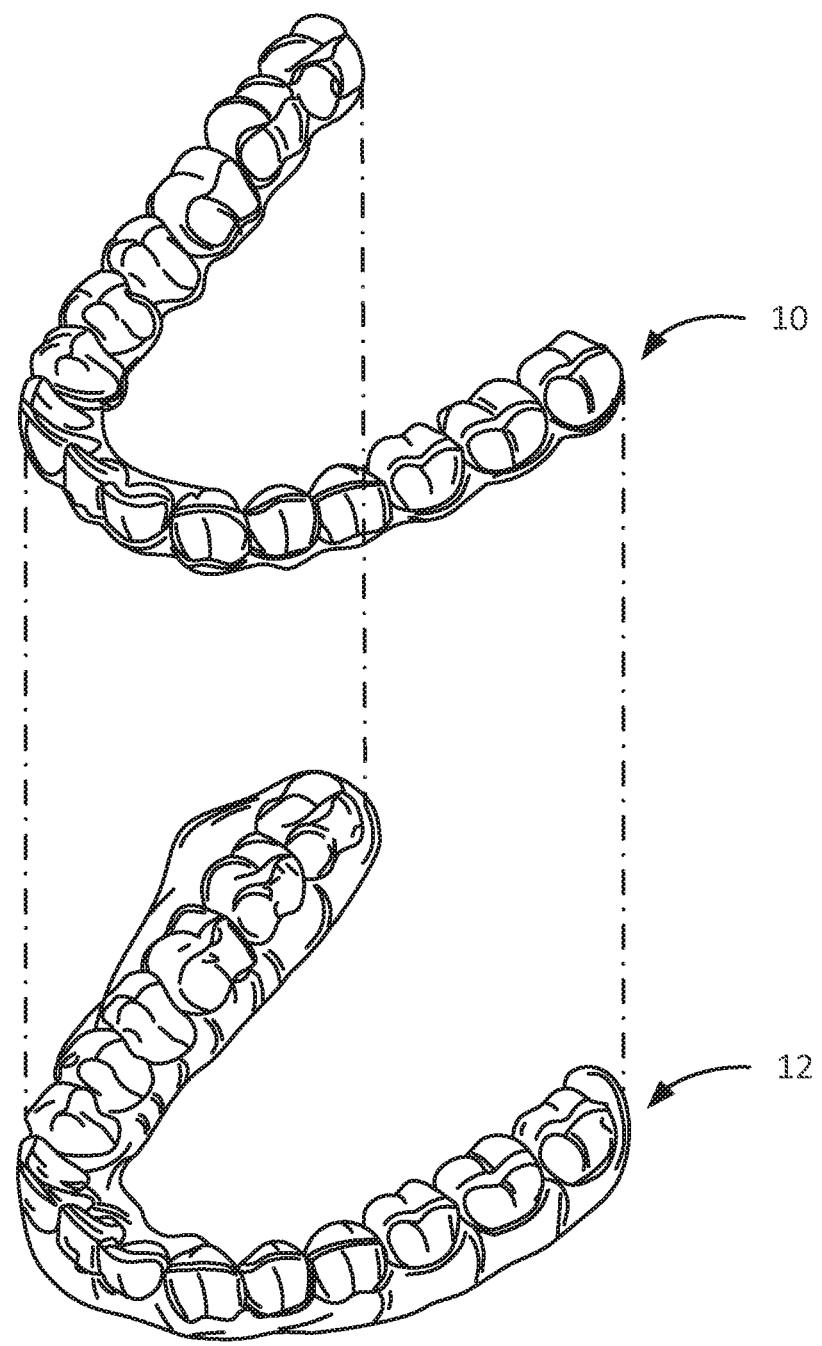
FIG. 1 illustrates a jaw and an incremental positioning appliance for the jaw, in accordance with an embodiment of the present invention.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Multilayer orthodontic positioning appliances are provided, as well as related methods and systems. During orthodontic treatment, it may be necessary to apply forces to a tooth to generate movement of the tooth to, for example, bring the patient's teeth into a better occlusion in a mesial or distal direction. The presently disclosed appliances, methods, and systems provide means by which such forces can be applied during orthodontic treatment where appliances having teeth receiving cavities are used, such as preformed appliances/aligners available from Align Technology, Inc., San Jose, Calif., under the trade name Invisalign® System. As provided by the present invention, the aligners that include multilayer sheets can, for example, provide increased durability of the aligners so that they can better withstand wear due to aligner reinsertion and removal and other mechanical stresses put on the aligner during treatment. In addition, the aligners have improved elastic properties that allow for less degradation in the shape of the teeth receiving cavities during a stage of treatment. For example, during a multistage orthodontic treatment, the force exerted by an aligner to perform defined tooth movement can degrade and may cause the treatment to include more aligners to reach a final ideal arrangement and/or result in a mid-course correction that could be prevented by using aligners with improved physical properties, such as those provided herein.

In one embodiment, the present invention provides a dental appliance for positioning a patient's teeth. The dental appliance can include a removable orthodontic tooth positioning appliance having teeth receiving cavities shaped to directly receive at least some of the patient's teeth and apply a resilient positioning force to the patient's teeth, the appliance comprising a hard polymer layer disposed between a first soft polymer layer and a second soft polymer layer.

In another embodiment, the present invention provides an orthodontic system for positioning a patient's teeth. The orthodontic system can include a plurality of incremental position adjustment appliances having teeth receiving cavities shaped to directly receive at least some of the patient's teeth and apply a resilient positioning force to the patient's teeth, wherein the appliances are successively worn by a patient to move teeth from one arrangement to a successive arrangement, and wherein at least one of the appliances comprises a hard polymer layer disposed between a first soft polymer layer and a second soft polymer layer.

In yet another embodiment, the present invention provides a method of making a dental appliance for positioning a patient's teeth. The method can include providing a sheet comprising a hard polymer layer of polymeric material disposed between a first soft polymer layer and a second soft polymer layer, providing a positive model of the patient's teeth in a target position; and fabricating an appliance as a negative of the positive model comprising thermoforming the sheet over the positive model.

Referring now to the drawings, in which like reference numerals represent like parts throughout the several views, FIG. 1 provides an appropriate starting point in a detailed discussion of various embodiments of the present invention with respect to tooth repositioning appliances designed to apply repositioning forces to teeth. A tooth repositioning appliance 10 can be worn by a patient in order to achieve an incremental repositioning of individual teeth in the jaw 12. The appliance can include a shell (e.g., a polymeric shell) having teeth-receiving cavities that receive and resiliently reposition the teeth. In many embodiments, a polymeric appliance can be formed from a sheet of suitable layers of polymeric material. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url invisalign.com").

An appliance can be designed and/or provided as part of a set of a plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

In general, structures, methods and systems of the present invention utilize a multilayer sheet for use in orthodontic appliances. The multilayer sheet can include three layers, in which a hard polymer layer is disposed between two soft polymer layers. The multilayer sheets used in the present invention can be used in making dental aligners having improved durability for use, e.g., to the elastic properties of the multilayer sheet when formed into an aligner. In addition, the bonding strength between the layers further improves the durability of the aligners, for example, by withstanding teeth grinding by a patient.

Figure 2:
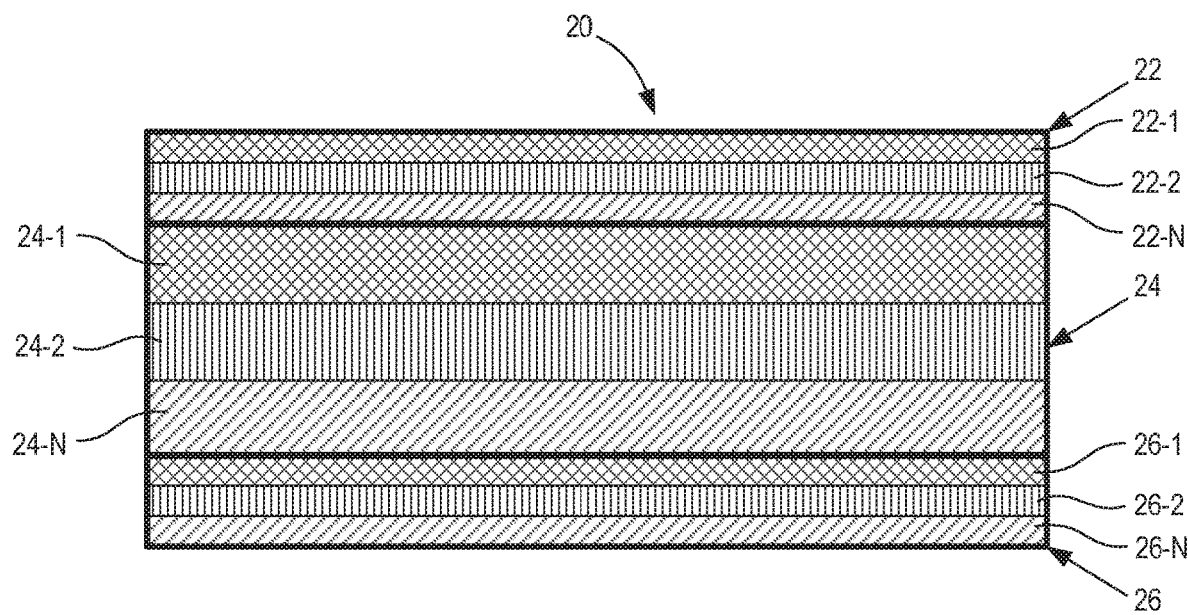
FIG. 2 shows an arrangement of polymer layers in a sheet having a hard polymer layer disposed between two soft polymer layers, in accordance with an embodiment of the present invention.

FIG. 2 shows a multilayer structure according to the present invention. As shown, a multilayer sheet 20 can include a three layer structure: a hard polymer layer 24 and two soft polymer layers 22, 26. The hard polymer layer can be disposed between a first soft polymer layer and a second soft polymer layer. In some embodiments, the hard polymer layer can be thicker than either of the soft polymer layers. The soft polymer layers can have the same or different thicknesses. For example, the hard polymer layer can have a thickness in a range from about 400 µm to about 1100 µm, about 450 µm to about 1000 µm, about 500 µm to about 900 µm, or about 550 µm to about 750 µm. The soft polymer layers can have a thickness in a range from about 25 µm to about 100 µm, about 30 µm to about 90 µm, or about 35 µm to about 80 µm. Multilayer sheets used for making appliances having a hard polymer layer disposed between two soft polymer layers can range from a thickness of about 500 µm to about 1200 µm, about 550 µm to about 1100 µm, or about 600 µm to about 1000 µm. In some embodiments, the thicknesses of the various layers can be tailored for a particular stage of treatment for the patient.

Suitable polymeric materials for the hard polymer layer can include a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof (e.g., a blend of at least two of the listed hard polymeric materials). In some embodiments, the hard polymer layer of the appliances can include polymeric materials, such as a polycarbonate, a co-polyester, a polyester, and a thermoplastic polyurethane. In some embodiments, the hard layer can be composed of multiple hard layers, e.g., two or three hard polymer layers 24-1, 24-2, 24-N co-extruded to form one hard layer.

The hard polymer layer of the appliances of the present invention can have a variety of physical properties that can, e.g., improve treatment options for a practitioner. For example, physical properties such as tensile strength, elongation at yield, elongation at break, tensile modulus, flexural modulus, stress relaxation over time, and light transmission can each be specifically tailored for a particular application. In some embodiments, the hard polymer layer of the appliances can have a physical property of at least one of a tensile strength at yield of between about 4000 pounds per square inch (psi) and 6500 psi, an elongation at yield of greater than about 4%, an elongation at break of greater than about 70%, a tensile modulus of greater than about 150,000 psi, a flexural modulus greater than about 150,000 psi, a stress relaxation at 24 hours testing in a wet environment (e.g., between about 90%-100% relative humidity) is greater than 10%, and a light transmission between 400 nm and 800 nm of greater than about 75%.

Suitable polymeric materials for the soft polymer layers of the appliance can include a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyimide elastomer, or a combination thereof (e.g., a blend of at least two of the listed soft polymeric materials). The soft polymer layers can be the same material or a different material. In certain embodiments, the first soft polymer layer and the second soft polymer layer are the same polymeric material.

The soft polymer layers of the appliances can have a variety of physical properties. For example, physical properties such as hardness, ultimate tensile strength, elongation at break, tensile modulus, compression set, flexural modulus, and light transmission can each be specifically tailored for a particular application. In some embodiments, the soft polymer layers of the appliances can independently have a physical property of at least one of a hardness of about 60 A to about 85 D, an ultimate tensile strength of greater than about 5000 psi, an elongation at break of greater than about 200%, a compression set at about 70° C. of greater than 40% after 24 hours, a flexural modulus of greater than about 35,000 psi, and a light transmission between 400 nm and 800 nm of greater than about 75%.

As described herein, the layers of the appliances can include a hard polymer layer disposed between two soft polymer layers. In one embodiment, the multilayer appliances can include a hard polymer layer of one type of material (e.g., a co-polyester), and two soft polymer layers of other types of material that can be the same or different (e.g., two soft polymer layers of thermoplastic polyurethane elastomer). In some embodiments, the multilayer appliances can also include a hard polymer layer of at least two layers of polymer material. For example, the hard polymer layer can include several polymer layers laminated together to form the hard polymer layer. The laminated hard polymer layer can include at least two layers of any combination of the following polymer materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetheritnide, a poiyethersulfone, and a polytrimethylene terephthalate. Similarly, in some embodiments, the multilayer appliances can include a soft polymer layer of at least two layers of polymer material. For example, the soft polymer layers 22, 26 can include a layer of several polymer layers 22-1, 22-2, 22-N and 26-1, 26-2, 26-N, respectively, laminated together. The laminated soft polymer layers can include at least two layers of any combination of the following polymer materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and a thermoplastic polyamide elastomer.

The tooth positioning appliances can be fabricated using a variety of methods. For example, methods for making the appliances can include thermoforming a multilayer sheet into an aligner by heating the sheet and then molding the sheet to a particular configuration. Exemplary methods for fabricating the appliances, including those utilized in the Invisalign® System, are described in numerous patents and patent applications assigned to Align Technology, Inc. including, for example, in U.S. application Ser. No. 13/186, 374 as well as on the company's website, which is accessible on the World Wide Web (see, e.g., the url invisalign.com").

Figure 3:
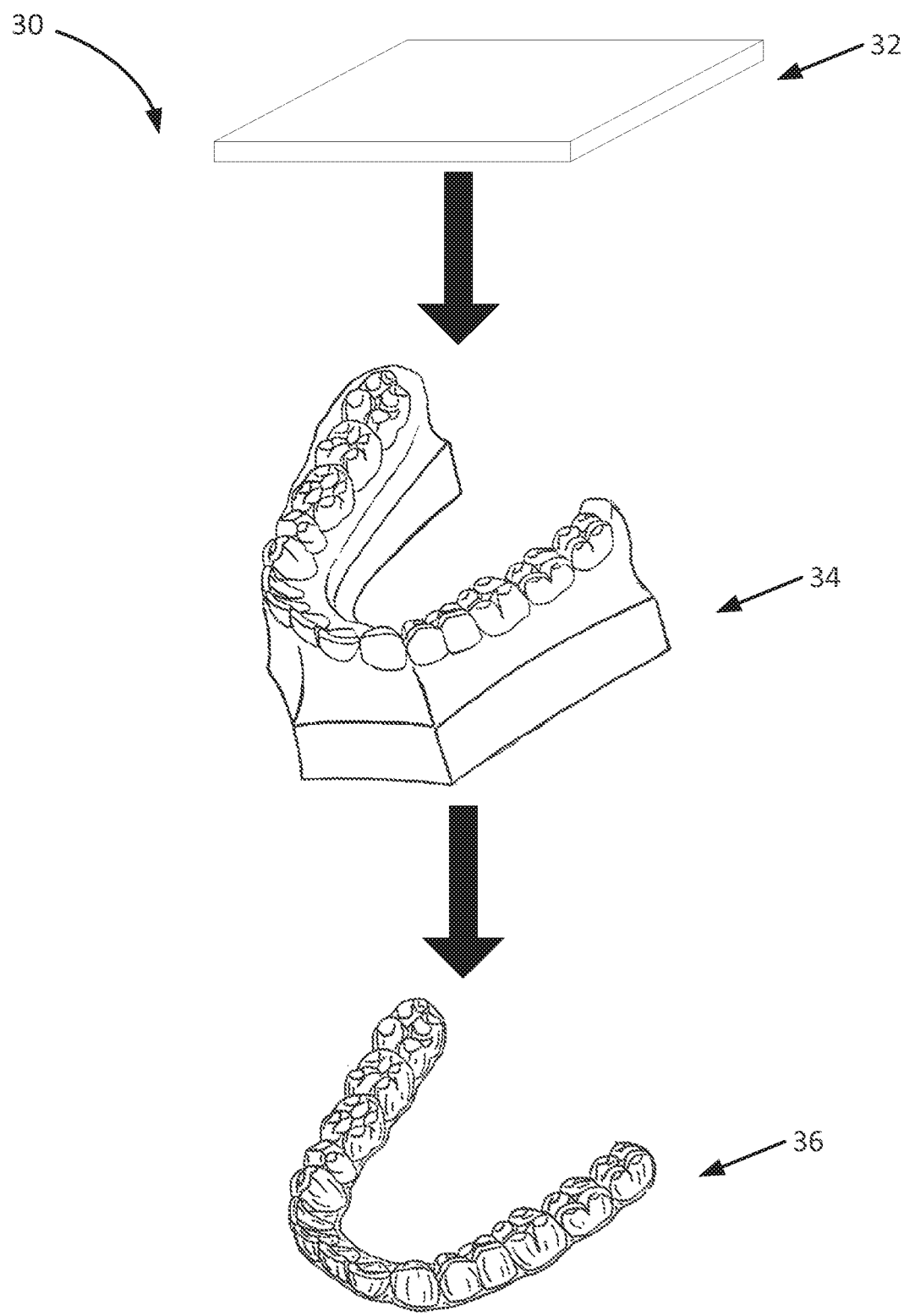
FIG. 3 depicts a method of making a multilayer dental appliance, in accordance with an embodiment of the present invention.

FIG. 3 depicts an example embodiment of a process 30 for forming a multilayer tooth positioning appliance, in accordance with an embodiment of the present invention. As shown, a multilayer sheet 32 can be formed into a tooth positioning appliance 36. The multilayer sheet 32, as depicted, can include three layers: a hard polymer layer disposed between two soft polymer layers. In this example process, the tooth positioning appliance 36 can be produced with the use of a physical tooth model, or mold, 34. The tooth positioning appliance 36 can be produced by heating the thermoformable multilayer sheet 32 and then vacuum or pressure forming the sheet over the teeth in the physical tooth model 34. The tooth positioning appliance 36 is a direct representation of the physical tooth model. Excess material from the sheet can be trimmed to form a final tooth positioning appliance that can be used for orthodontic treatment of a patient.

One or a series of physical tooth models, such as the model described above, may be used in the generation of elastic repositioning appliances for orthodontic treatment. Similar to the process above, each of the appliances can be generated by thermoforming a multilayer polymeric material over a mold of a desired tooth arrangement to form a dental appliance. The tooth positioning appliance of the desired tooth arrangement generally conforms to a patient's teeth but is slightly out of alignment with the initial tooth configuration. Placement of the elastic positioner over the teeth applies controlled forces in specific locations to gradually move the teeth into the desired configuration. Repetition of this process with successive appliances comprising new configurations eventually moves the teeth through a series of intermediate configurations to a final desired configuration.

Figure 4:
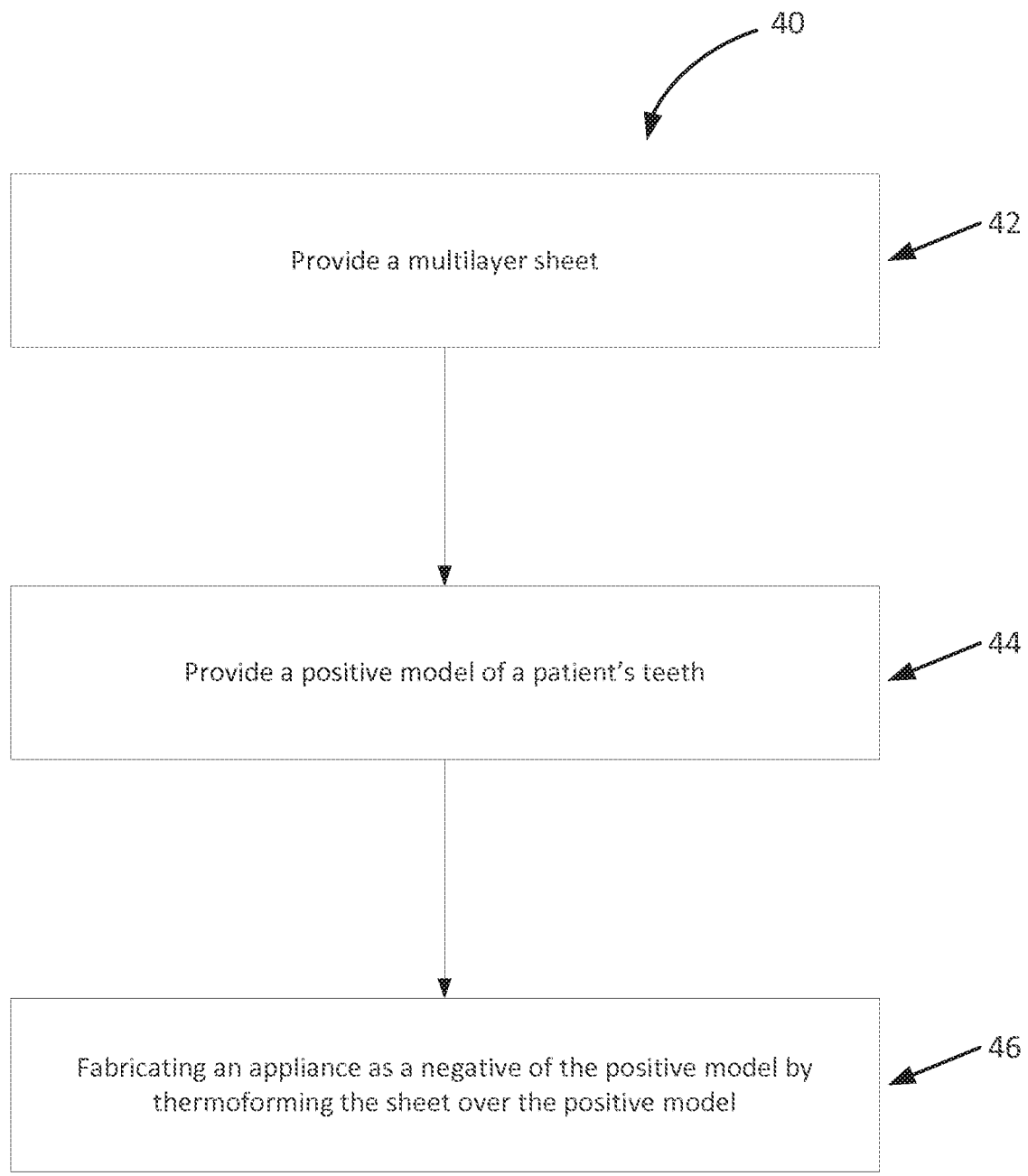
FIG. 4 is a simplified block diagram illustrating a method for fabricating a dental appliance, in accordance with an embodiment of the present invention.

The present invention includes a variety of methods for fabricating dental appliances. FIG. 4 shows a simple schematic for a method 40 of fabricating a removable orthodontic tooth positioning appliance having teeth receiving cavities shaped to directly receive at least some of the patient's teeth and apply a resilient positioning force to the patient's teeth, in accordance with an embodiment of the present invention. The method can include providing a multilayer sheet having a hard polymer layer disposed between two soft polymer layers (Step 42). The method can further include providing a positive physical model of a patient's teeth (Step 44). The tooth positioning appliance can be fabricated by thermoforming the multilayer sheet over the positive physical model (Step 46), in which the tooth positioning appliance is a negative of the positive model. As described above, the methods of fabrication can further include trimming or cutting portions of the sheet to render a final, usable appliance for orthodontic treatment.

Multilayer sheets of the present invention were analyzed and determined to provide a variety of improved properties for aligners used in orthodontic treatment. As further described herein, the multilayer sheets formed into aligners can, for example, provide increased durability of the aligners so that they can better withstand wear due to teeth grinding and other mechanical stresses put on the aligner during treatment. In addition, the aligners have improved elastic properties that allow for less degradation in the shape of the teeth receiving cavities during a stage of treatment. For example, during a multistage orthodontic treatment, the capability of an aligner to force tooth movement can degrade and may cause the treatment to include more aligners to reach a final ideal arrangement and/or result in a mid-course correction that could be prevented by using aligners with improved physical properties, such as those provided herein.

Figure 5:
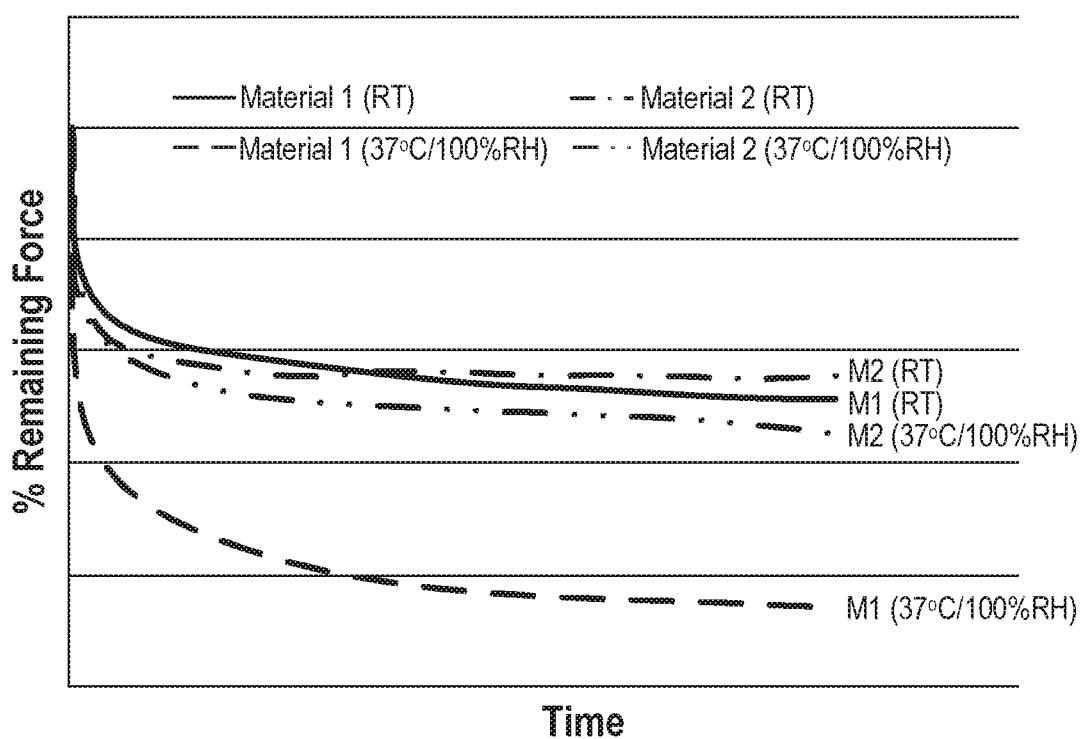
FIG. 5 provides a stress relaxation comparison for dental appliances, in accordance with an embodiment of the present invention.
Figure 6:
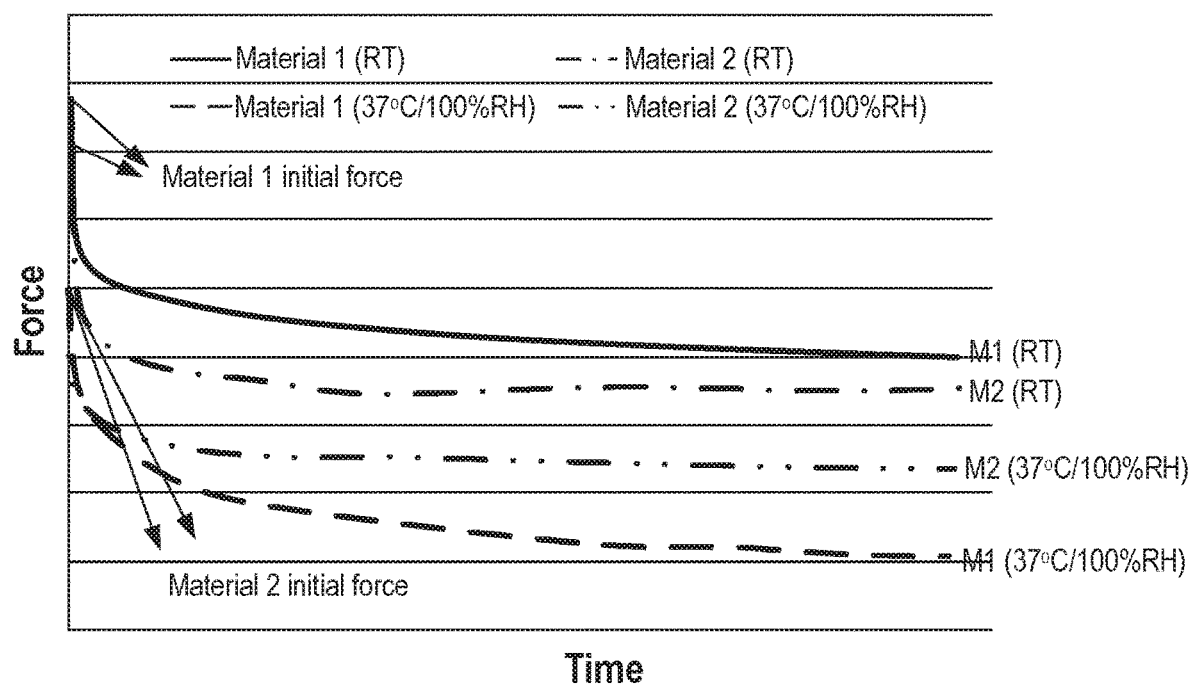
FIG. 6 provides another stress relaxation comparison for dental appliances, in accordance with an embodiment of the present invention.
Figure 7:
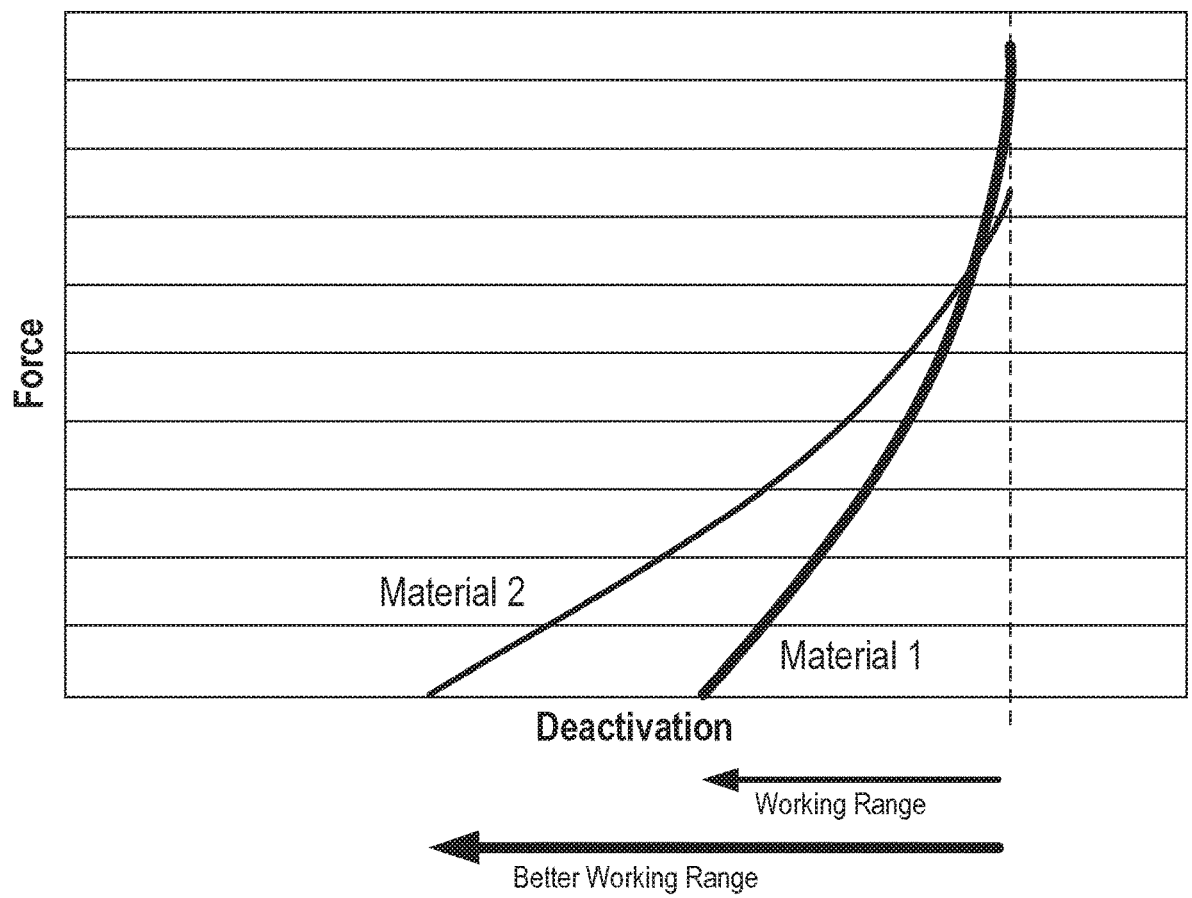
FIG. 7 shows a long-term unloading comparison for dental appliances, in accordance with an embodiment of the present invention.
Figure 8:
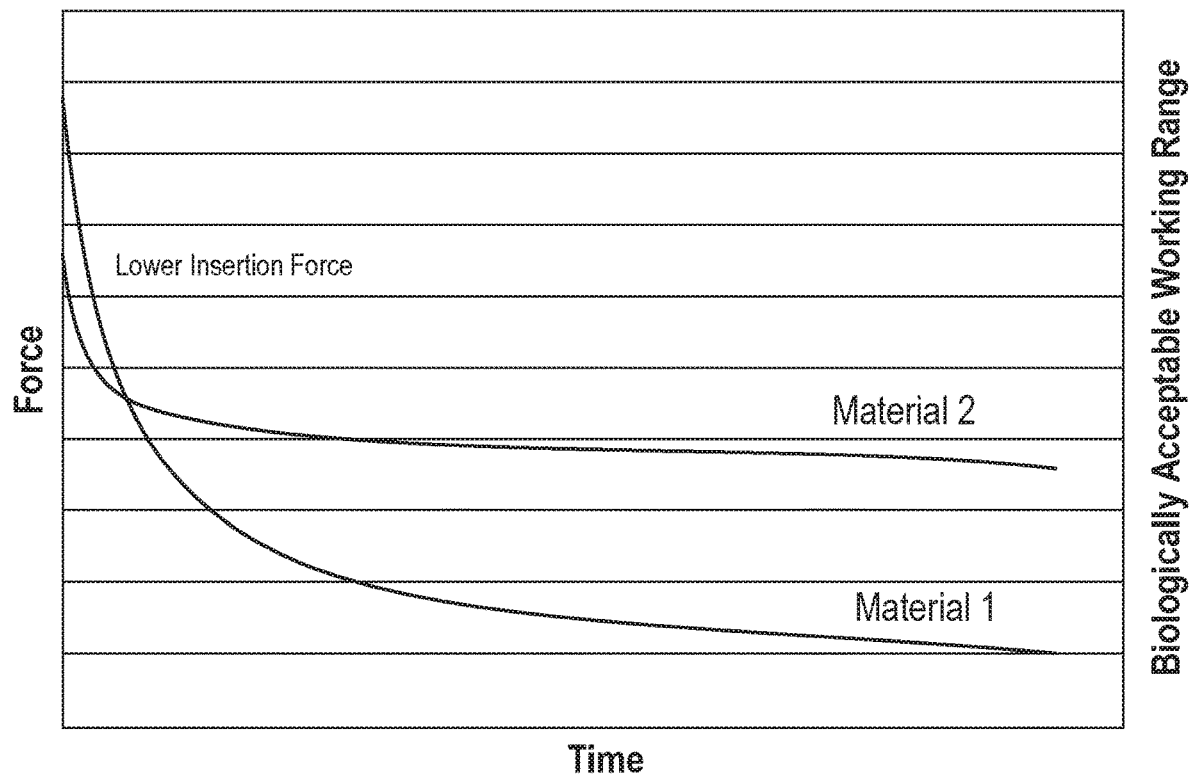
FIG. 8 provides a long-term movement comparison for dental appliances, in accordance with an embodiment of the present invention.

FIGS. 5-8 provide example test results that compare various physical properties of the multilayer sheet appliances of the present invention with other already existing aligner materials (Material 1). Samples of varied thicknesses were tested. For example, multilayer sheets were tested having a hard polymer layer with thicknesses ranging from about 580 μm to about 715 μm thick. In some examples, the hard layer was a co-polyester hard polymer layer. The soft layers tested ranged between about 50 μm to about 100 μm. In some examples, the hard polymer layer was disposed between thermoplastic polyurethane elastomer soft polymer layers. As shown in FIGS. 5 and 6, one example of the multilayer sheet material (Material 2) showed improved stress relaxation properties as compared to another already existing material (Material 1) at room temperature and at a 37° C./90-100% relative humidity condition. In addition, FIG. 7 shows improved long-term unloading characteristics of the multilayer sheet Material 2 versus the already existing Material 1 in a 37° C./90-100% relative humidity condition. The multilayer sheet showed less deflection under force loads. FIG. 8 also shows improved long-term movement data for the multilayer sheet Material 2 versus Material 1 in a 37° C./90-100% relative humidity condition.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Variations of the embodiments described herein may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A method of making a dental appliance for positioning a patient's teeth, the method comprising:
   providing a sheet comprising three or more polymer layers, the three or more polymer layers comprising:
      a hard polymer layer comprising a co-polyester and having a flexural modulus greater than about 150,000 psi; and
      a soft polymer layer comprising a thermoplastic polyurethane elastomer and having an elongation at break of greater than about 200%, and a hardness from about 60 A to about 85 D;
   providing a positive model of the patient's teeth in a target position; and
   fabricating an appliance as a negative of the positive model comprising thermoforming the sheet over the positive model.

2. The method of claim 1, wherein the hard polymer layer further comprises a polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, or a combination thereof.

3. The method of claim 1, wherein the hard polymer layer comprises at least two layers and the at least two layers each independently comprise a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, or a polytrimethylene terephthalate.

4. The method of claim 1, wherein the soft polymer layer further comprises a styrenic block copolymer, a silicone rubber, an elastomeric alloy, a thermoplastic elastomer, a thermoplastic vulcanizate elastomer, a block copolymer elastomer, a polyolefin blend elastomer, a thermoplastic co-polyester elastomer, a thermoplastic polyamide elastomer, or a combination thereof.

5. The method of claim 1, wherein the soft polymer layer comprises at least two layers, and wherein the at least two layers each independently comprise a styrenic block copolymer, a silicone rubber, an elastomeric alloy, a thermoplastic elastomer, a thermoplastic vulcanizate elastomer, a polyurethane elastomer, a block copolymer elastomer, a polyolefin blend elastomer, a thermoplastic co-polyester elastomer, or a thermoplastic polyamide elastomer.

6. The method of claim 1, wherein the hard polymer layer comprises at least one of a tensile strength at yield of between about 4000 psi and 6500 psi, an elongation at yield of greater than about 4%, an elongation at break of greater than about 70%, a tensile modulus of greater than about 150,000 psi, a stress relaxation greater than about 10% at 24 hours testing in a wet environment, and a light transmission between 400 nm and 800 nm of greater than about 75%.

7. The method of claim 1, wherein the soft polymer layer comprises at least one of an ultimate tensile strength of greater than about 5000 psi, a compression set at about 70° C. of greater than 40% after 24 hours, a flexural modulus of greater than about 35,000 psi, and a light transmission between 400 nm and 800 nm of greater than about 75%.

8. The method of claim 1, further comprising fabricating a plurality of appliances corresponding to different arrangements of the patient's teeth.

9. The method of claim 8, wherein fabricating the plurality of appliances comprises digitally staging a plurality of digital models of the patient's teeth and generating a plurality of physical models from the digital models.

10. The method of claim 8, wherein two or more of the plurality of appliances comprise a sheet comprising the hard polymer layer and the soft polymer layer.

11. The method of claim 1, wherein the hard polymer layer comprises a plurality of co-extruded or laminated polymer layers.

12. The method of claim 1, wherein the three or more polymer layers each comprise:
   co-polyester material having a flexural modulus greater than about 150,000 psi; or
   thermoplastic polyurethane elastomer material having an elongation at break of greater than about 200% and a hardness from about 60 A to about 85 D.

13. The method of claim 12, wherein the three or more polymer layers alternate between soft and hard polymer layers.

14. The method of claim 13, wherein the sheet has three polymer layers.

15. The method of claim 12, wherein the hard polymer layer is positioned adjacent to one or more soft polymer layers, the one or more soft polymer layers comprising the soft polymer layer.

16. The method of claim 1, wherein the hard polymer layer is disposed between the soft polymer layer and a second soft polymer layer, the second soft polymer layer comprising an elongation at break of greater than about 200% and a hardness from about 60 A to about 85 D.

17. The method of claim 1, wherein the appliance comprises a co-extruded material.

18. The method of claim 1, wherein the appliance comprises a thickness of between 500 μm and 1200 μm.

19. The method of claim 1, wherein the hard polymer layer comprises at least two layers and the at least two layers each independently comprise a polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, or a polytrimethylene terephthalate.

20. A method of making a plurality of dental appliances for positioning a patient's teeth, the method comprising:
   providing a sheet comprising three or more polymer layers, the three or more polymer layers comprising:
      a hard polymer layer comprising a co-polyester and having a flexural modulus greater than about 150,000 psi; and
      a soft polymer layer comprising a thermoplastic polyurethane elastomer and having an elongation at break of greater than about 200%, and a hardness from about 60 A to about 85 D;
   providing a plurality of positive models of the patient's teeth, each in a target position; and
   fabricating the plurality of dental appliances, each as a negative of at least one of the plurality of positive models comprising thermoforming the sheet over the at least one positive model.

21. The method of claim 20, wherein the hard polymer layer further comprises a polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, or a combination thereof.

22. The method of claim 20, wherein the soft polymer layer further comprises a styrenic block copolymer, a silicone rubber, an elastomeric alloy, a thermoplastic elastomer, a thermoplastic vulcanizate elastomer, a block copolymer elastomer, a polyolefin blend elastomer, a thermoplastic co-polyester elastomer, a thermoplastic polyamide elastomer, or a combination thereof.

\* \* \* \* \*